US006284453B1

(12) United States Patent
Siano

(10) Patent No.: US 6,284,453 B1
(45) Date of Patent: Sep. 4, 2001

(54) METHOD FOR CONTROLLING FERMENTATION GROWTH AND METABOLISM

(76) Inventor: Steven Anthony Siano, 10190 MacAdam La., Cupertino, CA (US) 95014

( * ) Notice: Subject to any disclaimer, the term of this patent is extended or adjusted under 35 U.S.C. 154(b) by 0 days.

(21) Appl. No.: 09/408,018

(22) Filed: Sep. 29, 1999

(51) Int. Cl.⁷ .............................. C12Q 1/02; C12N 1/00; G06F 19/00
(52) U.S. Cl. ................ 435/3; 435/29; 435/243; 702/19
(58) Field of Search ...................... 435/3, 29, 243; 702/19

(56) References Cited

U.S. PATENT DOCUMENTS

| | | | |
|---|---|---|---|
| 4,021,304 | 5/1977 | Shimamatsu et al. | 195/28 R |
| 5,595,905 | 1/1997 | Bishop et al. | 435/243 |
| 5,912,113 * | 6/1999 | Nakamura et al. | 435/3 |

FOREIGN PATENT DOCUMENTS 52-125686    10/1977    (JP) .

OTHER PUBLICATIONS

Sha Jin et al. J. Chem. tech. Biotechnol. 1994. vol. 64, pp. 273–281.*
Agrawal, (1989) Bioprocess Engineering. vol. 4, pp. 183–190.
Aiba et al. (1990). Biotechnology and Bioengineering. vol. 36, pp. 534–538.
Aiba et al. (1976) Biotechnology and Bioengineering. vol. 18, pp. 1001–1016.
Hibino et al. (1993). Journal of Fermentation and Bioengineering. vol. 75, No. 6, pp. 443–450.
Iversen et al. (1994) Appl. Microbiol. Biotechnol. 42:256–262.
Kurokawa et al. (1994). Biotechnol. Bioengineering. vol. 44, pp. 95–103.
Lounés et al. (1996) Process Biochemistry. vol. 31, No. 1, pp. 13–20.
Ozturk. (1996) Cytotechnology. 23:3–16.
Royce. (1992). Biotechnol. Bioengineering. vol. 40, pp. 1129–1138.
Siano. (1995). Biotechnology and Bioengineering. vol. 47, pp. 651–665.
Siano. (1996). Biotechnology and Bioengineering. vol. 52, pp. 713–717.
Siano. (1999) Biotechnology and Bioengineering. vol. 64, No. 6, pp. 755–758.

\* cited by examiner

*Primary Examiner*—Jon P. Weber
*Assistant Examiner*—Vera Afremova

(57) ABSTRACT

This invention is a method for controlling growth rate and metabolic state in fed-batch fermentations. Growth rate refers to the rate of exponential growth. Metabolic state refers to the relative consumption rates of the carbon and nitrogen sources. The method is based on a new use of the pH control reagent addition rate (RAR) and thus requires pH control and measurement of the RAR. The method also requires measurement of the oxygen uptake rate (OUR), or measurement of the biomass concentration (X) along with the reactor volume (V), or all three. Either the preferred embodiment or the first additional embodiment can be used when one metabolite limits growth and the metabolic state is determined by the organism through the growth rate. In the preferred embodiment, the controller feeds the growth-limiting metabolite such that the reagent-oxygen metabolic quotient, defined as RAR/OUR, is maintained at a set point corresponding to the desired growth rate. In the first additional embodiment, the controller feeds the growth-limiting metabolite such that the specific RAR, defined as RAR/XV, is maintained at a set point corresponding to the desired growth rate. A second additional embodiment can be used when two metabolites limit (growth and affect the metabolism. In this case, the multivariable controller feeds the two metabolites separately such that the specific RAR and the specific OUR, defined as OUR/XV, are maintained at a pair of set points corresponding to the desired growth rate and metabolic state.

6 Claims, 3 Drawing Sheets

METHOD FOR CONTROLLING FERMENTATION GROWTH AND METABOLISM

BACKGROUND OF THE INVENTION

This invention pertains to the control of growth and metabolism in fed-batch bioreactors.

The control of growth and metabolism is important because the maximum possible growth rate of an organism is often not the optimal growth rate in terms of process productivity. The maximum growth rate can easily be achieved and maintained by keeping all of the metabolites at high concentrations, but a process control method is needed when it is desired to maintain a growth rate that is lower than the maximum. In some cases, the maximum growth rate is optimal. But in these cases the metabolism may not be optimal because excess substrate may be metabolized to toxic or undesired byproducts. Thus, a method for controlling metabolism is needed. In short, the central goal in fermentation process engineering is to optimize a process by controlling growth and metabolism.

A primary object of the present invention and of fermentation process control in general is to maintain constant and optimal concentrations of the carbon and nitrogen sources in the growth medium so that the maximum possible specific product formation rate can be maintained for extended periods. In this way, the process yield and productivity can be improved or optimized for a process or a phase of the process and the batch-to-batch consistency can be improved. This general approach applies for any process, whether the product is a primary metabolite, a secondary metabolite, or the biomass itself.

The biological rationale behind this general approach is as follows:
1) The specific product formation rate depends on the relative activities of the organism's various metabolic pathways, which are regulated based on
2) The organism's energetic state and the relative intracellular availabilities of carbon and nitrogen, which are affected by
3) The organism's growth rate and metabolic state, which are affected by
4) The organism's consumption rates of the carbon and nitrogen sources, which are affected by
5) The concentrations of the carbon and nitrogen sources in the medium.

Thus, a process can be optimized by maintaining the carbon and nitrogen sources at concentrations associated with the maximum specific product formation rate.

This general approach to fermentation process control was shown for a fed-batch antibody process by H. Kurokawa et al., "Growth Characteristics in Fed-Batch Culture of Hybridoma Cells with Control of Glucose and Glutamine Concentrations," Biotechnol. Bioeng., Vol. 44, pp. 95–103 (1994). Antibody production was shown to depend on the growth rate and the metabolic state, i.e., the relative consumption rates of the carbon source glucose and the nitrogen source glutamine. The antibody production was improved by using at-line liquid chromatography to measure the concentrations of glucose and glutamine and by using an adaptive feeding algorithm to control these concentrations. By maintaining the optimal glucose and glutamine concentrations, growth and metabolism were controlled at points associated with a high product formation rate. However, at-line liquid chromatography is not fast enough or robust enough for routine industrial use.

The need for a more practical control method, based on this general approach, for a fed-batch antibiotic process was shown by A. Lounes et al., "Effect of Nitrogen/Carbon Ratio on the Specific Production Rate of Spiramycin by *Strepiornyces anibofaciens*," Process Biochemistry, Vol. 3 1, pp. 13–20 (1996). Spiramycin production was shown to depend on the growth rate and the metabolic state, i.e., the relative consumption rates of the carbon source glycerol and the nitrogen source ammonia. But without a practical control method, the maximum specific product formation rate was only maintained during a short phase of the process.

Other general approaches to improving product formation rates include
1) Using the best growth medium (carbon source, nitrogen source, precursors, and nutrients such as vitamins and minerals),
2) Using the optimal temperature, pH, redox potential, agitation rate, aeration rate, ionic strength, osmotic pressure, water activity, hydrostatic pressure, etc.,
3) Using the optimal dissolved oxygen or carbon dioxide concentration,
4) Using inducers and repressors,
5) Varying the above in a time-optimal fashion,
6) Minimizing the accumulation of byproducts that negatively impact the growth or metabolism of the organism,
7) Genetically altering the organism using recombinant DNA or hybridoma technology, and
8) Using auxotrophic mutants or mutants with altered regulatory systems.

The method of the present invention is not intended as a substitute for these environmental and genetic approaches, but as a complement.

Another general approach to fermentation process control is the use of continuous processes. Growth and metabolism are easily controllable in continuous bioreactors such as the chemostat, the pH-stat, and the RAR-stat. The latter was disclosed by H. Shimamatsu et al., "Process for Continuous Cultivation of Protein-Producing Microorganisms," U.S. Pat. No. 4,021,304 (May 3, 1977) and shown by P. Agrawal, "An Experimental Study of Acid Production Rate Controlled Operations of a Continuous Fermentor," Bioprocess Eng., Vol. 4, pp. 183–190 (1989), and is also referred to as an APR-stat (acid production rate). In continuous processes, the volume is constant because fresh medium is added at the same rate that broth (medium plus biomass) is withdrawn. Because of convection (flow through the system), steady state with respect to substrate, nutrient, biomass, and product concentrations, and thus growth and metabolism, is easily attainable. Growth and metabolism are controlled through the substrate and nutrient concentrations in the fresh medium and through the dilution rate for the chemostat, the buffering capacity of the fresh medium for the pH-stat, or the RAR set point for the RAR-stat (in all continuous processes, the growth rate equals the dilution rate at steady state). However, continuous fermentors are generally not used by industry because of various practical concerns such as the increased risk of contamination and the desire for batch downstream processing. Instead, fed-batch fermentors are preferred even though steady state is much harder to reach because of the lack of convection (in fed-batch reactors, the dilution rate is much less than the growth rate because concentrated feeds are used to minimize the increase in the volume).

Perhaps the most direct method to control growth and metabolism for fed-batch fermentors would involve on-line measurement and feedback control of substrate concentrations, i.e., a nutristat. But unfortunately, good (fast, accurate, robust, and autoclavable) substrate sensors are not yet available.

A promising but less direct method to control growth and metabolism is to use automated at-line measurements of the substrate concentrations. This was done, as discussed above, for glucose and glutamine using liquid chromatography and an adaptive feeding algorithm by H. Kurokawa et al., Biotechnol. Bioeng., Vol. 44, pp. 95–103 (1994). This was also done for glucose using a YSI Model 2000 analyzer and an algorithm for predicting the substrate consumption rate by B. F. Bishop et al., "Process Control System for Fed-Batch Fermentation Using a Computer to Predict Nutrient Consumption," U.S. Pat. No. 5,595,905 (Jan. 21, 1997). However, it is an object of the present invention to control fermentation growth and metabolism without measuring the concentrations of the growth-limiting metabolites.

Another method to control growth and metabolism is to feed the growth-limiting substrate according to an exponential schedule. However, this method is open-loop and does not have feedback, so overfeeding or underfeeding can occur at the beginning of the process if the biomass concentration is not estimated accurately, although eventually a constant growth rate may be reached.

Another method to control growth and metabolism is to feed the growth-limiting substrate in proportion to the measured total amount of biomass in the bioreactor, as shown by W. Hibino et al., "Three Automated Feeding Strategies of Natural Complex Nutrients Utilizing On-Line Turbidity Values in Fed-Batch Culture: A Case Study on the Cultivation of a Marine Microorganism," J. Ferm. Bioeng., Vol. 75, pp. 443–450 (1993). However, although this method is feedforward, it does not have feedback, so overfeeding can occur if the proportionality factor is not chosen properly.

Another method to control growth and metabolism is to feed the growth-limiting substrate such that the measured specific oxygen uptake rate (SOUR) is maintained at a set point corresponding to the desired growth rate. This method uses feedback and is effective when the SOUR is sufficiently sensitive, such as at low growth rates in which the growth- and nongrowth-associated components of oxygen uptake are comparable.

Another method to control growth and metabolism is to feed the growth-limiting substrate such that the measured respiratory quotient (RQ), defined as the carbon dioxide transfer rate (CTR) divided by the oxygen uptake rate (OUR), is maintained at a set point corresponding to the desired growth rate, as shown by S. Aiba et al., "Fed Batch Culture of *Saccharomyces cerevisiae*: A Perspective of Computer Control to Enhance the Productivity in Baker's Yeast Cultivation," Biotechnol. Bioeng., Vol. 18, pp. 1001–1016(1976) and S. Aiba et al., "Process for Growing Yeast in High Yield," Japanese Patent Laid-Open No. 52125686 (Oct. 21, 1977). This method uses feedback and is effective when the RQ is sufficiently sensitive, such as near the maximum growth rate in certain processes such as the aerobic yeast process, in which the undesired production of ethanol is indicated by an increase in the RQ.

BRIEF SUMMARY OF THE INVENTION

Accordingly, several objects and advantages of the present invention are to control fermentation growth and metabolism
1) In fed-batch processes,
2) By maintaining constant metabolite concentrations,
3) Using feedback to minimize or avoid overfeeding and underfeeding,
4) In a practical manner,
5) Using measurements that are fast, accurate, robust, and autoclavable, and
6) Without using on-line or at-line measurements of metabolite concentrations.

These objects and advantages are met in the present invention by basing the control method on the pH control reagent addition rate (RAR). The RAR is typically not measured or used for fermentation monitoring, much less control, because of a lack of understanding of the relationship between the RAR, growth, and metabolism. A new-found understanding of this relationship has made it possible to develop a new feedback control method based on the RAR, as disclosed herein. The objects and advantages are also met by combining the RAR with three known good measurements: the oxygen uptake rate (OUR), the biomass concentration (X), and the reactor volume (V).

The preferred embodiment of the present invention is most suited to fermentations in which one metabolite limits growth and the metabolic state is determined by the organism through the growth rate. A new parameter is developed for this type of process. This parameter is called the reagent-oxygen metabolic quotient (ROMQ), and is defined as RAR/OUR. The preferred embodiment takes advantage of the monotonic variation in the ROMQ versus the concentration of the growth-limiting metabolite. Feedback control is realized by feeding the metabolite such that the ROMQ is maintained at the set point corresponding to the desired growth rate. Thus, the growth rate is controlled through the ROMQ, which is controlled through the metabolite concentration, and the metabolic state is controlled through the growth rate.

The first additional embodiment of the present invention is also most suited to fermentations in which one metabolite limits growth and the metabolic state is determined by the organism through the growth rate. Another new parameter is developed for this type of process. This parameter is called the specific pH control reagent addition rate (SRAR), and is defined as RAR/XV. The first additional embodiment takes advantage of the monotonic variation in the SRAR versus the concentration of the growth-limiting metabolite. Feedback control is realized by feeding the metabolite such that the SRAR is maintained at the set point corresponding to the desired growth rate. Thus, the growth rate is controlled through the SRAR, which is controlled through the inetabolite concentration, and the metabolic state is controlled through the growth rate.

The second additional embodiment of the present invention is most suited to fermentations in which two metabolites limit growth and affect the metabolism. The second additional embodiment takes advantage of the different responses of the SRAR and the specific oxygen uptake rate (SOUR), defined as OUR/XV, to the metabolite concentrations. Multivariable feedback control is realized by feeding the two metabolites separately such that the SRAR and the SOUR are maintained at the pair of set points corresponding to the desired growth rate and metabolic state. The growth rate and metabolic state are controlled through the SRAR and the SOUR, which are controlled through the metabolite concentrations.

All three embodiments do not require on-line or at-line measurement of metabolite concentrations, but instead use measurements that are fast, accurate, robust, and autoclavable. Also, all three embodiments use feedback in a simple, practical manner that minimizes or avoids overfeeding and underfeeding. Finally, because of the feedback, all three embodiments are suitable for fed-batch processes; the convection advantage of continuous operation is not required to reach steady state.

DETAILED DESCRIPTION OF THE INVENTION

Reagent Addition Rate

Figure 1:
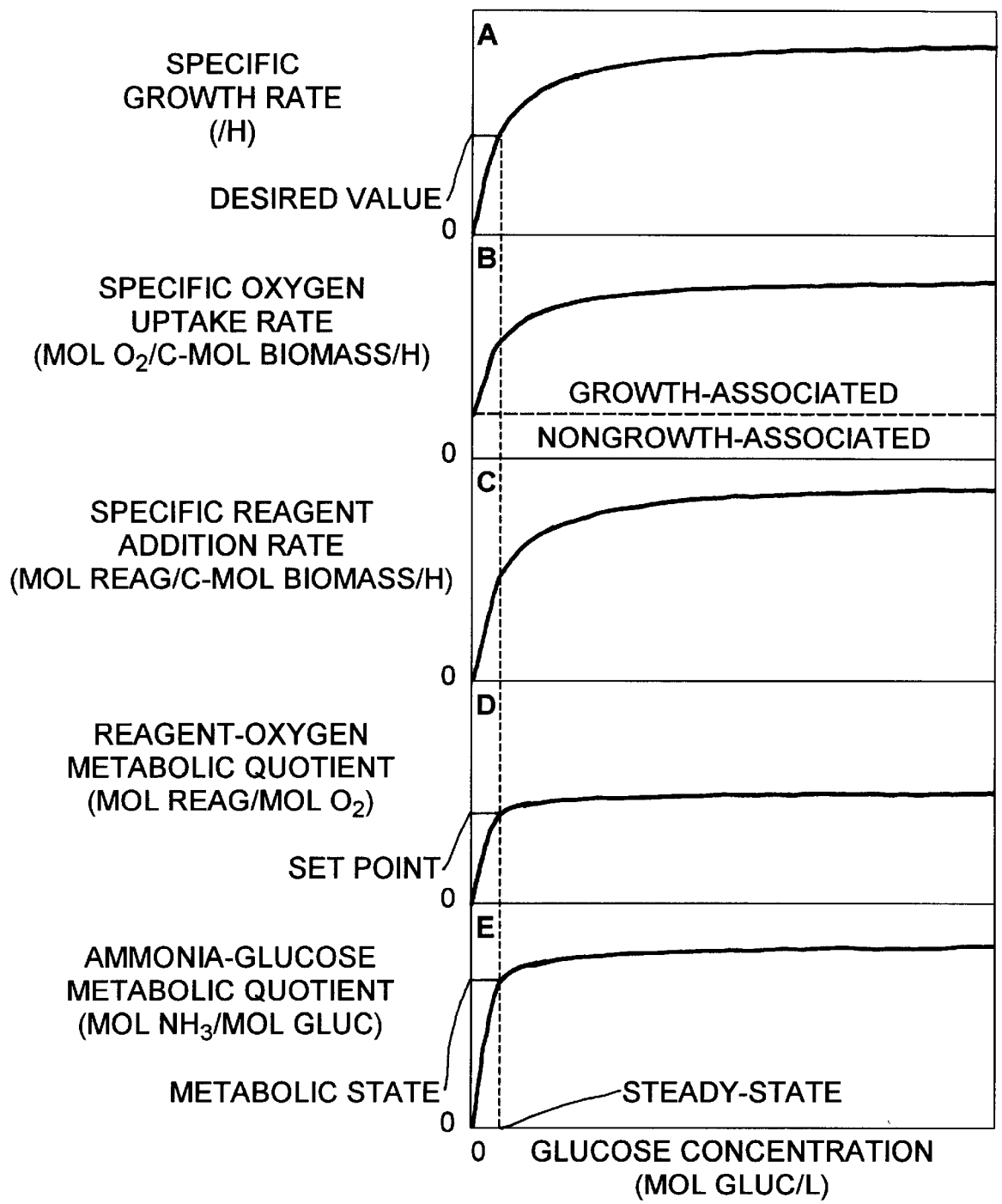
FIG. 1 shows how the reagent-oxygen metabolic quotient set point is related, through the glucose concentration, to the desired growth rate.

A distinguishing feature of all three embodiments of the present invention is the use of the pH control reagent addition rate (RAR) for feedback control of growth and metabolism.

The RAR (mol reag/h) is obtained by measuring the reagent flow rate:

$$RAR = F_{reag} C_{reag} \quad (1)$$

$F_{reag}$ reagent flow rate (L reag/h)
$C_{reag}$ reagent concentration (mol reag/L reag)
Here, $F_{reag}$ is a volumetric flow rate. The $F_{reag}$ can also be a mass flow rate if $C_{reag}$ is expressed in suitable units. The $F_{reag}$ can be measured by using any suitable volumetric or mass flow meter, or by using a load cell to measure the loss of weight from the reagent vessel, or by tracking the pulses of an ON-OFF pH controller.

Thus, the method of the present invention is practical since the RAR can be measured with standard equipment. New measurement technology, such as the on-line or at-line measurement of metabolite concentrations, is not required. Also, the RAR measurement is fast, accurate, and robust, and is not affected by the autoclaving or steam-sterilization of the fermentor.

The purpose of the remainder of this section is to teach the meaning of the RAR because the RAR is used in all three embodiments of the present invention. However, another practical aspect of the present invention is that a detailed understanding of the PAR and of growth and metabolism for the particular organism and process is not required to use the method of the present invention. Details regarding the RAR are shown by S. A. Siano, "On the Use of the pH Control Reagent Addition Rate for Fermentation Monitoring," Biotechnol. Bioeng., Vol. 47, pp. 651–665 (1995), with erratum at Vol. 49, p. 480 (1996), "Use of the Abiotic Proton Balance for Determining Linear Relations Among Net Conversion Rates of Primary Metabolites in Fermentation Processes," Biotechnol. Bioeng., Vol. 52, pp. 713–717 (1996), and "Use of the Abiotic Proton Balance for Describing the pH-Auxostat," Biotechnol. Bioeng., Vol. 64, pp. 755–758 (1999).

When the organism is consuming or producing a pH-affecting metabolite, the RAR required to maintain a constant pH is $$RAR = g_{reag} f_{met} R_{met} \quad (2)$$

$g_{reag}$ proportionality constant for proton neutralization (mol reag/mol H$^+$)
$f_{met}$ proportionality constant for proton formation (mol H$^+$/mol met)
$R_{met}$ metabolic rate for the pH-affecting metabolite (mol met/h)
By convention, $R_{met}$ is negative for consumption and positive for production.

For example, if NaOH is the pH control reagent and lactic acid is the only pH-affecting metabolite, then $$RAR = F_{NaOH} C_{NaOH}$$

$$= g_{NaOH} f_{lact\ acid} R_{lact\ acid}$$

At any pH set point above 5.9, each lactic acid produced by the organism and transported across the cell membrane into the medium will dissociate into lactate and a proton (H$^+$) because the pH is much greater than the pK$_\alpha$ for lactic acid (3.9). Thus, $f_{lact\ acid}$=1 mol H$^+$/mol lact acid. For each H$^+$ formed, the pH controller must add one hydroxyl (OH$^-$) to neutralize the H$^+$ and bring the pH back up to the set point. Because NaOH is a strong base, each NaOH will contribute one OH for proton neutralization, i.e., $g_{NaOH}$=1 mol NaOH/mol H$^+$. Thus, in this simple example, RAR=$R_{lact\ acid}$.

Likewise, if the process liberates ammonia (NH$_3$) from amino acid consumption and the pH is controlled at any set point below pH 7.3 using HCl, then RAR=$R_{NH3}$ because $g_{HCl}$=-1 mol HCl/mol H$^+$ and $f_{NH3}$=-1 mol H$^+$/mol NH$_3$. Because the pH is much less than the pK$\alpha$ for NH$_4^+$ (9.3), each NH$_3$ produced by the organism and transported across the cell membrane into the medium will associate with a proton to form NH$_4^+$ (ammonium), requiring the addition of one H$^+$ to replace the associated H$^+$ and bring the pH back down to the set point. Because HCl is a strong acid, each HCl will contribute one H$^+$ for proton replacement.

By similar reasoning, if lactic acid is being consumed and HCl is used to control the pH, then RAR=-$R_{lact\ acid}$, and if NH$_3$ is being consumed and NaOH is used to control the pH, then RAR=-$R_{NH3}$.

Note that since $g_{reag}$ is the proportionality constant for proton neutralization, it is positive for a base ($g_{NaOH}$=1 mol NaOH/mol H$^+$) and negative for an acid ($g_{HCl}$=-1 mol HCl/mol H$^+$). Also, note that since $f_{met}$ is the proportionality constant for proton formation, it is positive for an acid ($f_{lact\ acid}$=1 mol H$^+$/mol lact acid) and negative for a base ($f_{NH3}$=-1 mol H$^+$/mol NH$_3$).

If the pH and pK$_\alpha$ values differ by about 2 units or more, then the $f_{met}$ values are integers, as shown above for lactic acid and ammonia. Other examples, provided the fermentor pH is 6.8 or higher, include $f_{acet\ acid}$=1 mol H$^+$/mol acet acid (for acetic acid, pK$_\alpha$=4.8) and $f_{but\ acid}$=1 mol H$^+$/mol but acid (for butyric acid, pK$_\alpha$=4.8).

But if the pH and pK$_\alpha$ values differ by less than about 2 units, then the $f_{met}$ values should be determined experimentally by adding a known amount of a solution containing the metabolite to the medium at the desired pH set point and temperature and measuring the amount of reagent required to return the pH to its original value, i.e., $$f_{met} = \frac{C_{reag} V_{reag}}{g_{reag} C_{met} V_{met}} \quad (3)$$

$V_{reag}$ volume of reagent used in the experiment (L reag)
$C_{met}$ concentration of pH-affecting metabolite (mol met/L solution)
$V_{met}$ volume of pH-affecting metabolite used in the experiment (L solution)
For example, if the pH setpoint is 5.5, then $f_{acet\ acid}$ will be less than 1 and must be determined experimentally. If 1 mL of 0.75 M acetic acid solution is added to the medium at pH 5.5, the pH will drop. If 2.84 mL of 0.20 M NaOH is required to bring the pH back up to 5.5, then $$f_{acet\ acid} = \frac{0.20\frac{mol\,NaOH}{L\,reag}0.00284\frac{L\,reag}{1\frac{mol\,NaOH}{mol\,H^+}0.75\frac{mol\,acet\ acid}{L\,acet\ acid\,sol}0.001\frac{L\,acet\ acid\,sol}{}}}$$

$$= 0.76\frac{mol\,H^+}{mol\,acet\ acid}$$

The volume of the medium used in the experiment is irrelevant except that it must be small enough such that the pH measurements have adequate sensitivity.

Another example is citric acid, which has three $pK_\alpha$ values: 3.1, 4.8, and 6.4. If the pH setpoint is 5.5, then $f_{cit\ acid}$ will be around 2 and must be determined experimentally. If 1 mL of 0.30 M citric acid solution is added to the medium at pH 5.5, the pH will drop. If 3.05 mL of 0.20 M NaOH is required to bring the pH back up to 5.5, then $$f_{cit\ acid} = \frac{0.20\frac{mol\,NaOH}{L\,reag}0.00305\frac{L\,reag}{1\frac{mol\,NaOH}{mol\,H^+}0.30\frac{mol\,cit\ acid}{L\,cit\ acid\,sol}0.001\frac{L\,cit\ acid\,sol}{}}}$$

$$= 2.03\frac{mol\,H^+}{mol\,cit\ acid}$$

Likewise, the $g_{reag}$ values are often ratios of integers, as shown above for NaOH and HCl. Other examples include $g_{H2SO4}=-½$ mol $H_2SO_4$/mol $H^+$ (for sulfuric acid) and $g_{Ca(OH)2}=½$ mol $Ca(OH)_2$/mol $H^+$ (for calcium hydroxide). This is because most pH control reagents are strong acids or strong bases. If necessary, the $g_{reag}$ can be determined experimentally by first determining $f_{reag}$ for the reagent as discussed above and then using $$g_{reag} = -1/f_{reag} \quad (4)$$

For example, if $f_{NH3}=-1$ mol $H^+$/mol $NH_3$, then $g_{NH3}=1$ mol $NH_3$/mol $H^+$.

The $f_{met}$ and $g_{reag}$ values generally do not change during the process because they are not affected by the buffering capacity of the medium and because the effect of changes in ionic strength during the process is typically negligible.

The RAR due to $CO_2$ production (evolution) requires an additional term to account for the dynamics of the bicarbonate buffer system:

$$RAR = g_{reag}f_{CO2}(CER - CTR) \quad (5a,b)$$

$$= g_{reag}f_{CO2}CER\left(1 - \frac{CTR}{CER}\right)$$

$f_{CO2}$ proportionality constant for proton formation (mol $H^+$/mol $CO_2$)

CER $CO_2$ evolution rate (mol $CO_2$/h), i.e., the metabolic rate for $CO_2$

CTR $CO_2$ transfer rate (mol $CO_2$/h), i.e., the rate measured for $CO_2$ by off-gas analysis As shown in Eq. (5a), the RAR is only affected by the accumulation of $CO_2$ in the bicarbonate buffer system of the medium, i.e., the difference between the $CO_2$ evolution rate (into the medium) and the $CO_2$ transfer rate (from the medium to the gas phase and out of the fermentor). The CTR is what is measured by off-gas analysis. The CER is the true metabolic rate, but it can not be measured directly. The pH-affecting reaction is the dissociation of carbonic acid ($H_2CO_3$) to a proton ($H^+$) and the bicarbonate ion ($HCO_3^-$). Carbonic acid is formed by the reaction of $CO_2$ and water.

When CTR/CER is close to one, i.e., when (1–CTR/CER) is close to zero, the RAR due to $CO_2$ accumulation is negligible versus the RAR due to the other primary pH-affecting metabolites. A CTR/CER close to one is desired for simplicity and is the case in most aerobic processes because the rate of $CO_2$ mass transfer is high relative to the growth rate. However, CTR/CER is not close to one in unsparged anaerobic processes and in certain aerobic processes with low rates of $CO_2$ mass transfer (low rates of agitation and aeration) relative to the growth rate. One example is when the process is aerated using the tubing method.

Fortunately, even if CTR/CER is less than one, it is still a constant for exponentially growing cultures, as shown theoretically by S. Aiba and H. Furuse, "Some Comments on Respiratory Quotient (RQ) Determination from the Analysis of Exit Gas from a Fermentor," Biotechnol. Bioeng., Vol. 36, pp. 534–538 (1990) and as shown theoretically and experimentally by P. N. Royce, "Effect of Changes in the pH and Carbon Dioxide Evolution Rate on the Measured Respiratory Quotient of Fermentations," Biotechnol. Bioeng., Vol. 40, pp. 1129–1138 (1992). This was also shown theoretically by J. J. L. Iversen et al., "On-Line Growth Measurements in Bioreactors by Titrating Metabolic Proton Exchange," Appl. Microbiol. Biotechnol., Vol. 42, pp. 256–262 (1994), who also showed experimentally that $f_{CO2}$(1–CTR/CER) is a constant for exponentially growing cultures. All three investigators showed that (1–CTR/CER) increases with increasing pH. For example, if (1–CTR/CER) equals 0.16 at pH 5 for a process that is poorly agitated and aerated, then it equals about 0.5 at pH 7 for this same process. Furthermore, $f_{CO2}$ increases with increasing pH. For example, if $f_{CO2}$ equals 0.08 mol $H^+$/mol $CO_2$ at pH 5 for a certain growth medium and temperature, then it equals about 0.90 mol $H^+$/mol $CO_2$ at pH 7 for this same medium and temperature. In general, $f_{CO2}$ equals 0.5 mol $H^+$/mol $CO_2$ at a pH of about 6.3.

Thus, in processes with a high rate of $CO_2$ mass transfer relative to the growth rate, the RAR required to neutralize the proton formation from $CO_2$ accumulation is negligible, regardless of the pH. In processes with a low rate of $CO_2$ mass transfer relative to the growth rate, the RAR required to neutralize the proton formation from $CO_2$ accumulation is not negligible and increases with increasing pH because of both the increase in (1–CTR/CER) and the increase in $f_{CO2}$ with increasing pH.

The effect of $CO_2$ accumulation on the RAR during the exponential growth phase can be determined experimentally by running the process under standard conditions and at higher mass transfer rates (higher rates of agitation, or aeration, or both) and measuring RAR/OUR and CTR/OUR during exponential growth. The RAR/OUR will decrease (if the reagent is a base) or increase (if the reagent is an acid) with increasing mass transfer rates, eventually leveling off when CTR/CER equals one. The subscript high will be used below for the case of high mass transfer, i.e., when CTR/CER equals one. The CTR/CER during standard conditions is determined using $$\left(\frac{CTR}{CER}\right)_{standard} = \frac{\left(\frac{CTR}{OUR}\right)_{standard}}{\left(\frac{CER}{OUR}\right)_{standard}} = \frac{\left(\frac{CTR}{OUR}\right)_{standard}}{\left(\frac{CTR}{OUR}\right)_{high}} \quad (6)$$

Once $(CTR/CER)_{standard}$ is known, the $f_{CO2}$ is determined using $$f_{CO2} = \frac{\left(\frac{RAR}{OUR}\right)_{standard} - \left(\frac{RAR}{OUR}\right)_{high}}{g_{reag}\left(\frac{CTR}{OUR}\right)_{standard}\left[\left(\frac{CER}{CTR}\right)_{standard} - 1\right]} \quad (7)$$

For example, if the measured CTR/OUR during exponential growth is 0.90 mol $CO_2$/mol $O_2$ under standard conditions and 1.13 mol $CO_2$/mol $O_2$ with high mass transfer, then $$\left(\frac{CTR}{CER}\right)_{standard} = \frac{0.90 \frac{mol\ CO_2}{mol\ O_2}}{1.13 \frac{mol\ CO_2}{mol\ O_2}} = 0.80$$

And, if $g_{reag}$=1 mol reag/mol $H^+$ and the measured RAR/OUR during exponential growth is 0.30 mol reag/minol $O_2$ under standard conditions and 0.25 mol reag/mol $O_2$ with high mass transfer, then $$f_{CO2} = \frac{0.30 \frac{mol\ reag}{mol\ O_2} - 0.25 \frac{mol\ reag}{mol\ O_2}}{1 \frac{mol\ reag}{mol\ H^+} 0.90 \frac{mol\ CO_2}{mol\ O_2}\left[\frac{1}{0.80} - 1\right]}$$

$$= 0.22 \frac{mol\ H^+}{mol\ CO_2}$$

Also, the RAR can be affected by a feed that is not at the same pH as the fermentor:

$$RAR = g_{reag} f_{feed} F_{feed} \quad (8)$$

$f_{feed}$ proportionality constant for proton formation due to a feed (mol $H^+$/L feed)

$F_{feed}$ flow rate of pH-affecting feed (L feed/h)

The $f_{feed}$ will be positive for an acidic feed (relative to the medium) and negative for a basic feed (relative to the medium).

Generally, $f_{feed}$ should be determined experimentally:

$$f_{feed} = \frac{C_{reag} V_{reag}}{g_{reag} V_{feed}} \quad (9)$$

$V_{feed}$ volume of pH-affecting feed used in the experiment (L feed)

For example, if the pH setpoint is 5.5, then $f_{feed}$ for a feed of 0.75 M acetic acid and 0.75 M sodium acetate will be less than 1 and must be determined experimentally. If 1 mL of feed is added to the medium at pH 5.5, the pH will drop. If 2.50 mL of 0.20 M NaOH is required to bring the pH back up to 5.5, then $$f_{feed} = \frac{0.20 \frac{mol\ NaOH}{L\ reag} - 0.00250 \frac{L\ reag}{1 \frac{mol\ NaOH}{mol\ H^+} 0.001 \frac{L\ feed}{}}}$$

$$= 0.50 \frac{mol\ H^+}{L\ feed}$$

As is the case with $f_{met}$ and $g_{reag}$, $f_{feed}$ generally does not change during the process. But, for the sake of simplicity, it is best to use feeds that do not affect the RAR.

The RAR values in Eqs. (2), (5), and (8) do not depend on the buffering capacity of the medium because the $f_{met}$, $f_{CO2}$, $f_{feed}$, and $g_{reag}$ values do not depend on the buffering capacity. Thus, the various pH-affecting reactions act independently with respect to the RAR, and they can be combined as follows:

$$RAR = g_{reag}\left[\sum f_{met} R_{met} + f_{CO2} CER\left(1 - \frac{CTR}{CER}\right) + \sum f_{feed} F_{feed}\right] \quad (10)$$

Eq. (10) is referred to as the abiotic proton balance (APB). The subscript met refers to all of the primary pH-affecting metabolites except $CO_2$. The APB applies to batch, fed-batch, perfusion, and continuous reactors.

Nomenclature

The following terms are used to describe the method of the present invention. A set of units is given, but any other set of units is just as appropriate.

X viable biomass concentration (C-mol biomass/L)
S substrate concentration (mol sub/L)
F flow rate (L/h)
V liquid volume in the fermentor (L)
D dilution rate (/h), equals F/V
R metabolic rate for the entire fermentor (mol met/h), negative for consumption, positive for production
RAR reagent addition rate (mol reag/h), positive
SRAR specific reagent addition rate (mol reag/C-mol biomass–h), equals RAR/XV
OUR oxygen uptake rate (mol $O_2$/h), positive, equals $-R_{O2}$
SOUR specific oxygen uptake rate (mol $O_2$/C-mol biomass–h), equals OUR/XV
GUR glucose uptake rate (mol gluc/h), positive, equals $-R_{gluc}$
SGUR specific glucose uptake rate (mol gluc/C-mol biomass–h), equals GUR/XV
AUR ammonia uptake rate (mol $NH_3$/h), positive, equals $-R_{NH3}$
SAUR specific ammonia uptake rate (mol $NH_3$/C-mol bloinass–h), equals ALR/XV
GlnUR glutamine uptake rate (mol gln/h), positive, equals $-R_{gln}$
SGlnUR specific glutamine uptake rate (mol gln/C-mol biomass–h), equals GlnUR/XV
ROMQ reagent-oxygen metabolic quotient (mol reag/mol $O_2$), equals RAR/OUR and SRAR/SOUR
AGMQ ammonia-glucose metabolic quotient (mol $NH_3$/mol gluc), equals AUR/GUR and SAUR/SGUR
GlnGMQ glutamine-glucose metabolic quotient (mol gln/mol gluc), equals GlnUR/GUR and SGlnUR/SGUR
$\mu$ specific growth rate (C-mol bioinass/C-mol biomass–h), referred to as growth rate (/h) by convention, equals $R_{biomass}$/XV Growth in fed-batch fermentors is described using the known equation $$XV = X_0 V_0 \exp(\mu t)$$

The total amount of biomass in the bioreactor (XV) increases exponentially with time (t) at the specific growth rate $\mu$ (the total amount of biomass at time zero is $X_0 V_0$).

Preferred Embodiment

EXAMPLE 1

In this example, the carbon source is glucose and the nitrogen source is ammonia. The growth is limited by glucose. The ammonia is in excess and does not limit growth.

This example is typical of many fermentations, including yeast.

The pH-affecting metabolite in this example is ammonia; CTR/CER is assumed to equal one and thus $CO_2$ evolution will not affect the RAR. The pH control reagent in this example is ammonia. The pH is less than 7.3, $g_{NH3}=1$ mol $NH_3$/mol H, and $f_{NH3}=-1$ mol $H^+$/mol $NH_3$.

FIG. 1 shows how the glucose concentration S affects growth and metabolism according to the known Monod model for growth and the known Herbert-Pirt model for metabolism. These models are used only for illustration; the method of the present invention does not depend in any way on the models. The Monod model is used to represent the known increase in $\mu$ with increasing S. The Herbert-Pirt model is used to represent the known growth-associated and nongrowth-associated components of oxygen and glucose consumption. The nongrowth-associated component is also commonly referred to as the maintenance component because it is used to maintain the living state, as opposed to being used for growth. The total consumption rate, for oxygen and for glucose, is simply the sum of the growth-associated and nongrowth-associated components.

FIG. 1A shows how S affects $\mu$.

FIG. 1B shows how S affects the SOUR. The nongrowth-associated component becomes larger relative to the growth-associated component as S decreases.

FIG. 1C shows how S affects the SRAR. For this example, $$RAR = g_{NH3} f_{NH3} R_{NH3}$$
$$= AUR$$

Thus, the reagent ammonia addition rate equals the metabolite ammonia uptake rate (AUR) since $g_{NH3}=1$ mol $NH_3$/mol $H^+$, $f_{NH3}=-1$ mol $H^+$/mol $NH_3$, and the metabolic rate for ammonia, $R_{NH3}$, is negative because the ammonia is being consumed.

FIG. 1D shows how S affects the ROMQ. This relationship is monotonic, and has higher sensitivity at lower S, because the SOUR has a nongrowth-associated component but the SRAR does not. Without this component, the ROMQ would be a constant and would not depend on S.

FIG. 1E shows how S affects the ammonia-glucose metabolic quotient (AGMQ=AUR/GUR), which is used here to represent the metabolic state, i.e., the relative consumption rates of the nitrogen source ammonia and the carbon source glucose. As with the ROMQ, this relationship is monotonic, and has higher sensitivity at lower S, because the SGUR has a nongrowth-associated component but the SAUR does not. Without this component, the AGMQ would be a constant and would not depend on S.

Feedback control of growth and metabolism is realized in this example by feeding glucose such that the ROMQ is maintained at a set point corresponding to the desired ,, as shown in FIGS. 1A and 1D. The S is maintained at a steady-state value corresponding to both the desired $\mu$ and the ROMQ set point, as shown in FIG. 1E. In this example, the metabolic state (the AGMQ) is determined by the organism through the growth rate, as shown in FIG. 1E.

Feedback is especially beneficial at low $\mu$ in this example because overfeeding and underfeeding would cause large fluctuations in both $\mu$ and the AGMQ.

The method of the present invention can be used to optimize a phase of a process as follows. First, RAR, OUR, and productivity data are acquired for an uncontrolled batch process. From this transient data, an ROMQ value corresponding to high productivity is found. This value will be used as the initial ROMQ set point. Then, the new fed-batch process is run under feedback control using the initial ROMQ set point. Other fed-batch experiments are run using set points near the initial value. The productivity data from the fed-batch runs is used to determine the optimal ROMQ set point, which corresponds to the optimal values of $\mu$ and S. Thus, a detailed understanding of the RAR and of growth and metabolism for the particular organism and process is not required. Instead, the optimal ROMQ set point may simply be found by trial and error. The method is still based on the abiotic proton balance (APB) and the monotonic variation of the ROMQ with S, but the various pH control, growth, and metabolic parameters need not be known. These include the $g_{reag}$, $f_{met}$, $f_{CO2}$, and CTR/CER of the RAR equation (the APB), and for this example, the Monod growth parameters and the Herbert-Pirt metabolic parameters.

EXAMPLE 2

This example is the same as Example 1, except that the organism produces acetic acid at high S. This undesired byproduct negatively impacts growth and metabolism, and its accumulation should be minimized or avoided. The carbon source is glucose and the nitrogen source is ammonia. The growth is limited by glucose. The ammonia is in excess and does not limit growth.

This example is typical of many fermentations, including recombinant *Escherichia coli*.

The pH-affecting metabolites in this example are ammonia and acetic acid; CTR/CER is assumed to equal one and thus $CO_2$ evolution will not affect the RAR. The pH control reagent in this example is NaOH. The pH is less than 6.8, $g_{NaOH}=1$ mol NaOH/mol $H^+$, $f_{NH3}=-1$ mol $H^+$/mol $NH_3$, and it has been determined experimentally, for the given pH, medium, and temperature, that $f_{acet\ acid}=0.72$ mol $H^+$/mol acet acid.

Figure 2:
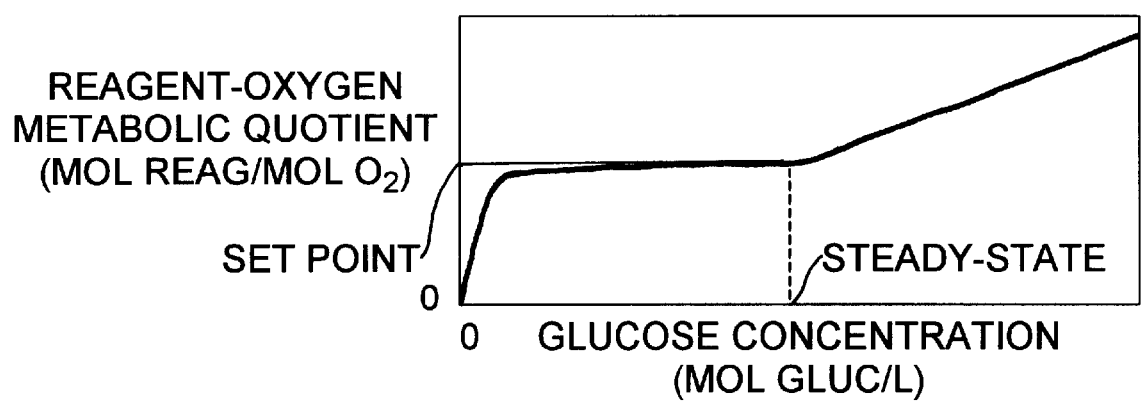
FIG. 2 shows that the reagent-oxygen metabolic quotient is sensitive at high glucose concentrations if the organism produces an acid at high glucose concentrations.

FIG. 2 shows that the ROMQ is more sensitive at high S in this example, versus Example 1, because of the acid production.

For this example, $$RAR = g_{NaOH}(f_{NH3}R_{NH3} + f_{acet\ acid}R_{acet\ acid})$$
$$= AUR + 0.72\ APR$$

APR acetic acid production rate (mol acet acid/h)

As with Example 1, feedback control of growth and metabolism is realized in this example by feeding glucose such that the ROMQ is maintained at a set point corresponding to the desired $\mu$. The S is maintained at a steady-state value corresponding to both the desired $\mu$ and the ROMQ set point, as shown in FIG. 2. As with Example 1, the metabolic state (the AGMQ) is determined by the organism through the growth rate.

Feedback is especially beneficial at high S in this example because overfeeding would cause acetic acid production and underfeeding would cause slow growth. Through feedback, the process can be maintained near the maximum $\mu$ while minimizing or avoiding the undesired acid production.

As with Example 1, the initial ROMQ set point can be determined from batch data and the optimal ROMQ set point can be determined through fed-batch experiments.

As cited in the Background Of The Invention, the measured respiratory quotient (RQ), defined as CTR/OUR, was used for feedback control of yeast at high 1 by S. Aiba et al., Biotechnol. Bioeng., Vol. 18, pp. 1001–1016 (1976) and Japanese Patent Laid-Open No. 52125686 (Oct. 21, 1977).

The RQ applied because the yeast produced ethanol at high $\mu$, and the ethanol production was accompanied by $CO_2$ evolution. Because of the feedback, the process could be maintained near the maximum $\mu$ while minimizing or avoiding the undesired ethanol production.

Summary.

Thus, a new parameter, the ROMQ, has been defined based on an understanding of the relationship between the RAR, growth, and metabolism, and based on an understanding of the relationship between S, growth, and metabolism. And, this new parameter can be used in a new way to provide feedback control of growth and metabolism in fed-batch fermentations. Because of the feedback, substrate overfeeding and underfeeding can be minimized or avoided and the substrate concentration can be maintained at the desired optimal value.

First Additional Embodiment

EXAMPLE 1

This example is the same as Example 1 above except that feedback control of growth and metabolism is realized by feeding glucose such that the SRAR of FIG. 1C is maintained at a set point corresponding to the desired $\mu$.

EXAMPLE 2

This example is the same as Example 2 above except that feedback control of growth and metabolism is realized by feeding glucose such that the SRAR is maintained at a set point corresponding to the desired $\mu$.

Summary.

Thus, a new parameter, the SRAR, has been defined for use in a new way to provide feedback control of growth and metabolism in fed-batch fermentations.

Second Additional Embodiment

EXAMPLE 3

In this example, glucose is a carbon source, glutamine is both a carbon source and a nitrogen source (a carbon-nitrogen source), and ammonia is a nitrogen source. The growth is limited by both glucose and glutamine, which both affect the metabolism. The ammonia is in excess, does not limit growth, is consumed when glucose is used for biomass formation, and is released when glutamine is used for biomass formation or for maintenance. The net effect of the ammonia reactions is that ammonia is produced by the culture.

This example is typical of many fermentations, including Streptomyces (here, glutamine is used simply to represent the complex, economical protein source used in Stieptornyces processes).

The pH-affecting metabolite in this example is ammonia; CTR/CER is assumed to equal one and thus $CO_2$ evolution will not affect the RAR. The pH control reagent in this example is HCl. The pH is less than 7.3, $g_{HCl}=-1$ mol HCl/mol H$^+$, and $f_{NH3}=-1$ mol H$^+$/mol $NH_3$.

Figure 3:
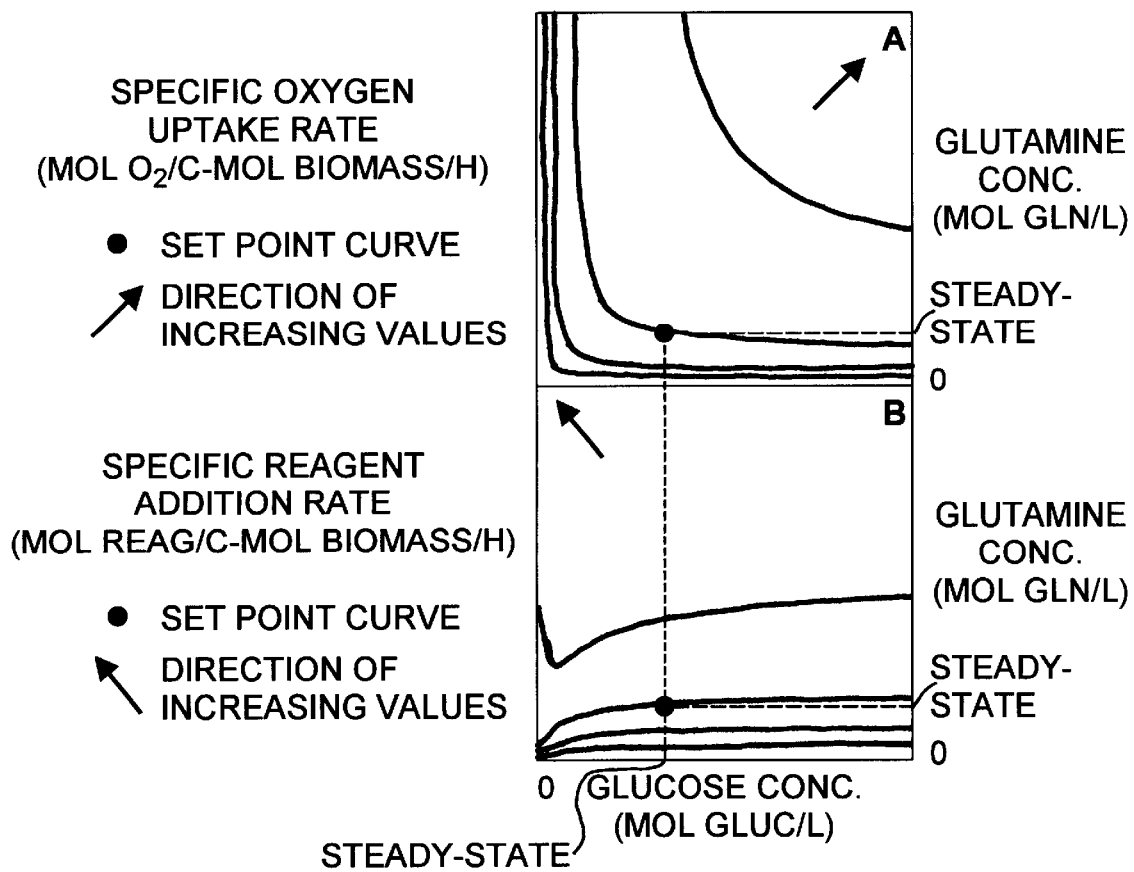
FIG. 3 shows that the intersection of the specific oxygen uptake rate and the specific reagent addition rate set point curves corresponds to only one pair of glucose and glutamine concentrations.

FIG. 3 shows how the glucose concentration $S_1$ and the glutamine concentration $S_2$ affect the SOUR and the SRAR (according to the known double-Monod model).

The plots in FIG. 3 are contour plots. For example, in FIG. 3A each curve represents a constant SOUR, the SOUR increment between curves is the same, and the arrow shows the direction of increasing SOUR.

FIG. 3A shows how $S_1$ and $S_2$ affect the SOUR. This relationship is monotonic with respect to $S_1$ and $S_2$ and has higher sensitivity at lower $S_1$ and $S_2$. As shown by the arrow in FIG. 3A, the SOUR increases with increasing $S_1$ and increasing $S_2$.

FIG. 3B shows how $S_1$ and $S_2$ affect the SRAR. For this example, $$RAR = g_{HCl}f_{NH3}R_{NH3}$$

$$= AER$$

AER ammonia evolution rate (mol $NH_3$/h)

Again, this relationship is monotonic with respect to $S_1$ and $S_2$ and has higher sensitivity at lower $S_1$ and $S_2$. But more importantly, the SRAR responds differently than the SOUR to changes in both $S_1$ and $S_2$. As shown by the arrow in FIG. 3B, the SRAR increases with decreasing SI and increasing $S_2$.

In this example, the metabolic state is represented by the glutamine-glucose metabolic quotient (GlnGMQ=GlnUR/GUR), i.e., the relative consumption rates of the carbon-nitrogen source glutamine and the carbon source glucose.

Multivariable feedback control of growth and metabolism is realized in this example by feeding glucose and glutamine such that the SOUR and the SRAR are maintained at a pair of set points corresponding to the desired $\mu$ and GlnGMQ. The SOUR and SRAR set points are actually curves, and these curves intersect at only one pair of $S_1$ and $S_2$, as shown in FIG. 3, which corresponds to only one pair of $\mu$ and the GlnGMQ (not shown). The $S_1$ and $S_2$ are maintained at steady-state values corresponding to both the desired $\mu$-GlnGMQ pair and the SOUR-SRAR set point pair, as shown in FIG. 3. Feedback control is made possible by the different responses of the SOUR and the SRAR to $S_1$ and $S_2$, as shown in FIGS. 3A and 3B, in which the arrows are almost orthoganol.

In this example, it may be best to control the SOUR by feeding glucose and to control the SRAR by feeding glutamine since for Streptomyces the SRAR is typically more sensitive to $S_2$ whereas the SOUR is typically equally sensitive to $S_1$ and $S_2$.

Feedback is especially beneficial at low $\mu$ in this example because overfeeding and underfeeding would cause large fluctuations in both $\mu$ and the GlnGMQ.

As with Examples 1 and 2, the initial SOUR and SRAR set points can be determined from batch data and the optimal SOUR and SRAR set points can be determined through fed-batch experiments.

EXAMPLE 4

This example is the same as Example 3, except that the organism produces lactic acid when S is above a critical value. This undesired byproduct negatively impacts growth and metabolism, and its accumulation should be minimized or avoided. Glucose is a carbon source, glutamine is a carbon-nitrogen source, and ammonia is a nitrogen source. The growth is limited by both glucose and glutamine, which both affect the metabolism. The ammonia is in excess, does not limit growth, is consumed when glucose is used for biomass formation, and is released when glutamine is used for biomass formation or for maintenance. The net effect of the ammonia reactions is that ammonia is produced by the culture.

This example is typical of many mammalian cell fermentations.

The pH-affecting metabolites in this example are ammonia, $CO_2$, and lactic acid; CTR/CER is significantly less than one and thus $CO_2$ evolution will affect the RAR. The pH control reagent in this example is a base (NaOH) because the combined effect of $CO_2$ evolution and lactic acid production exceeds the effect of ammonia production. The pH is 7.4, $g_{NaOH}$=1 mol NaOH/mol H$^+$, $f_{lact\ acid}$=1 mol H$^+$/mol lact acid, and it has been determined experimentally, for the given pH, medium, and temperature, that $f_{NH3}$=−0.98 mol H$^+$/mol NH3, $f_{CO2}$=0.96 mol H$^+$/mol $CO_2$, and CTR/CER=0.50.

For this example, $$RAR = g_{NaOH}\left[f_{NH3}R_{NH3} + f_{lact\ acid}R_{lact\ acid} + f_{CO2}CER\left(1 - \frac{CTR}{CER}\right)\right]$$
$$= -0.98\,AER + APR + 0.48\,CER$$

APR lactic acid production rate (mol lact acid/h)

The SRAR is more sensitive at high S in this example, versus Example 3, because of the acid production.

As with Example 3, multivariable feedback control of growth and metabolism is realized in this example by feeding glucose and glutamine such that the SOUR and the SRAR are maintained at a pair of set points corresponding to the desired 1 and GlnGMQ. The $S_1$ and $S_2$ are maintained at steady-state values corresponding to both the desired $\mu$-GlnGMQ pair and the SOUR-SRAR set point pair.

In this example, it may be best to control the SOUR by feeding glutamine and to control the SRAR by feeding glucose since for mammalian cells the SRAR is typically more sensitive to $S_1$ because of the lactic acid production whereas the SOUR is typically more sensitive to $S_2$.

Feedback is especially beneficial at high S in this example because overfeeding of glucose would cause lactic acid production and underfeeding would cause slow growth. Through feedback, the process can be maintained near the maximum 1 while minimizing or avoiding the undesired acid production.

As with Example 3, the initial SOUR and SRAR set points can be determined from batch data and the optimal SOUR and SRAR set points can be determined through fed-batch experiments.

Summary.

Thus, a new parameter, the SRAR, has been defined for use, along with the known SOUR, in a new way to provide multivariable feedback control of growth and metabolism in fed-batch fermentations. The SOUR can not be used by itself to control a process with two growth-limiting metabolites because the SOUR depends on the concentrations of both growth-limiting metabolites, as shown in FIG. 3A. The second additional embodiment of the present invention combines the SRAR with the SOUR in a new multivariable control method that relies on the differences in the responses of the SRAR and the SOUR to changes in the concentrations of the growth-limiting metabolites.

Process Control

Algorithm. The purpose of this section is to show that standard control algorithms may be used to adjust the feed rates based on the measured parameters. Advanced control methods are not required.

For example, for all three embodiments of the present invention, the standard proportional-integral (PI) control algorithm may be used for manipulating the feed rates, although any other control algorithm is just as appropriate. Also, discrete (sampled-data) control may be needed since the measurements may not be continuous. Finally, anti-reset windup may be needed since the controller may call for a negative feed rate at the beginning of the process. Thus, a possible control algorithm is $$F_{nT} = F_0(t) + K_c(t)e_{nT} + \frac{K_c(t)}{\tau_I}\sum(e_{nT}T) +$$
$$\frac{1}{\tau_I}\sum[(F^*_{(n-1)T} - F_{(n-1)T})T]$$

F feed rate calculated by the algorithm $F_0$ steady-state feed rate $K_C$ controller proportional gain (can be positive or negative)

e error (set point minus measured value) in the measured parameter (e.g., ROMQ, SRAR, SOUR, etc.)

n sample index (integer)

T sampling period $\tau_I$ controller integral time constant

F* actual feed rate (F*=0 if F≦0 and F*=F if F>0)

The steady-state feed rate $F_0$ may be held constant, as is standard practice in most control applications, or it may be increased exponentially based on the desired growth rate:

$$F_0(t)=F_0(t=0)\exp(\mu_D t)$$

$U_D$ desired growth rate (h$^{-1}$)

t time (h)

Thus, the control method of the present invention can be thought of as exponential fed-batch with the added feature of feedback based on the pH control reagent addition rate (RAR). Likewise, the controller proportional gain $K_C$ may be increased with time. One possibility is to increase $K_C$ exponentially, but at a lower rate than $F_0$:

$$K_C(t)=K_C(t=0)\exp(k\mu_D t)$$

k exponential increase factor for $K_C$ relative to $F_0$ (between 0 and 1)

Finally, for the multivariable control of the second additional embodiment, a relative gain calculation reveals that the interaction between the loops may not be significant and thus cross-controllers may not be required. If possible, cross-controllers should be avoided for the sake of simplicity, especially since the process is nonlinear.

Tuning.

Tuning (choosing $K_C$ and $\tau_I$) by trial and error may be the best approach since the process is nonlinear and the classical tuning rules do not apply.

Often, the organism can not respond immediately to changes in substrate concentrations. For example, there may be a lag in the $\mu$ response to an increase in S, and during this transient the organism may completely oxidize some of the excess substrate, causing the SOUR to increase, while spilling (wasting) the excess energy generated. As is standard practice in feedback control, these nonideal responses may be dealt with by decreasing $K_C$ and increasing $\tau_I$.

Also, for some organisms the growth-limiting substrate becomes inhibitory to growth at high concentrations. In this case, the controlled parameter (ROMQ, SRAR, or SOUR) may change directions at high S and will not be monotonic in the range of high S. Thus, it is important to keep S in its useful range, that is, the range in which the controlled parameter is monotonic. Again, this may be dealt with by decreasing $K_C$ and increasing $\tau_I$.

Finally, as with any feedback loop, the problem of measurement noise and measurement and control lags may be dealt with through smoothing (filtering) the data and by decreasing $K_C$ and increasing $\tau_I$. Since the method of the present invention uses a ratio of measured parameters as the controlled parameter, it may be important to make the measurement lags equal. This may be done by delaying the use of the faster measurement. Thus, the ratio will refer to a single point in time. Delaying the faster measurement will give increased stability at the expense of a slower response, which is a good trade-off.

Set Points.

As with any type of process, the set points can be varied with time during the process to account for various physiological changes of the organism or to optimize the various phases of the process such as lag, log, production, stationary, and death.

Feeds.

As with any fermentation feed, the feeds of the present invention may contain components other than the process control metabolite in order to prevent the depletion of any nutrients during the process. For example, if the ROMQ set point is maintained with a glucose feed, the feed may also contain phosphate or other nutrients so that glucose remains the growth-limiting metabolite.

Steady State.

In the method of the present invention, feedback control is used to attain steady state with respect to the metabolite concentrations, A, and the metabolic state, and to attain pseudo-steady state with respect to the feeds and the total amount of biomass in the bioreactor (XV). At pseudo-steady state, the feed rates and the total amount of biomass increase exponentially, signifying a constant $\mu$. This definition of pseudo-steady state is conventional for fed-batch fermentation processes.

Certain physiological changes can alter the relationship between S and the ROMQ (preferred embodiment), or between S and the SRAR (first additional embodiment), or between $S_1$ and $S_2$ and the SOUR and SRAR (second additional embodiment). When this occurs, the metabolite concentrations, $\mu$, and the metabolic state are maintained at the new values corresponding to the original set points. These physiological changes, such as changes in the Monod constant, and their effects are too detailed to discuss. But more importantly, these changes do not make the process unstable. Instead, the process will remain in control, but at a slightly different growth rate or metabolic state.

Fed-Batch Perfusion

In perfusion processes, cells are retained in the fermentor by various means, the volume is constant, and spent medium is removed from the fermentor at the same rate that either concentrated feeds or fresh medium are supplied. Because of the cell retention, the dilution rate D must increase in proportion to X in order to reach pseudo-steady state (the metabolite concentrations, $\mu$, and the metabolic state are constant while D and X increase exponentially), as shown by S. S. Ozturk, "Engineering Challenges in High Density Cell Culture Systems," Cytotechnology, Vol. 22, pp. 3–16 (1996). The relationship between D and p depends on the value of X versus $X_{cont}$, where $X_{cont}$ is the biomass concentration that would be obtained in a continous process at the same desired growth rate, metabolic state, and metabolite concentrations in the feed. When $X<X_{cont}$, $D<\mu$, and when $X>X_{cont}$, $D>\mu$ (of course, at the instant $X=X_{cont}$, $D=\mu$).

When concentrated feeds are used, $X_{cont}$ is large and thus D is small and is typically less than $\mu$. Thus, the process is like a fed-batch process and the feedback control method of the present invention can be used to control growth and metabolism. When fresh medium is used, D is larger and is typically greater than or equal to U. Thus, the process is like a continuous process, steady state is easily reached through convection, and the method of the present invention is not advantageous. The former case is useful when the goal is to wash out toxic byproducts using the lowest possible D. The latter case is useful when a higher D is required to wash out the toxic byproducts or when the product is chemically unstable and must be removed from the process to minimize degradation.

The former case, i.e, perfusion with concentrated feeds, is considered here to be a fed-batch process.

Conclusions, Ramifications, and Scope of the Invention

Three feedback methods that use the pH control reagent addition rate (RAR) have been developed for controlling growth and metabolism in fed-batch bioreactors. Because of the feedback, metabolite overfeeding and underfeeding can be minimized or avoided and the metabolite concentrations can be maintained at the desired optimal values. Thus, the methods can be used to optimize an entire process or any phase of the process and to improve batch-to-batch consistency.

The methods are also practical. The set points can be found by experiment. Also, a detailed understanding of the RAR and of growth and metabolism for the particular organism and process is not required. Furthermore, standard control algorithms such as proportional-integral can be used; advanced control methods are not required. And finally, the methods can be implemented using standard equipment; the RAR measurement does not require new measurement technology.

The methods use measurements that are fast, accurate, robust, and autoclavable. The new measurement, the RAR, is a physical measurement and does not involve chemical analysis. It simply requires the measurement of flow or weight or the tracking of the pulses of an ON-OFF pH controller. Thus, it is not affected by the steam-sterilization of the fermentor.

The methods also do not require on-line or at-line measurements of metabolite concentrations. These new measurement technologies were avoided by using the information in the RAR and by combining the RAR in new ways with available measurements such as the oxygen uptake rate, the biomass concentration, and the reactor volume.

The above description contains three embodiments and four examples. These should not be construed as limitations on the scope of the invention.

The preferred embodiment just requires a monotonic relationship between the reagent-oxygen metabolic quotient (ROMQ) and the metabolite concentration over a useful range of the metabolite concentration. The first additional embodiment just requires a monotonic relationship between the specific reagent addition rate (SRAR) and the metabolite concentration over a useful range of the metabolite concentration. The second additional embodiment just requires that the SRAR and the specific oxygen uptake rate (SOUR) are affected differently by the two metabolite concentrations such that a pair of SOUR and SRAR set points corresponds to only one pair of the two metabolite concentrations, and that these relationships hold over useful ranges of the two metabolite concentrations.

The first example considers aerobic growth on glucose, and the second example adds acetic acid production at high glucose concentrations. The third example considers aerobic growth on glucose and glutamine, and the fourth example adds lactic acid production at high glucose concentrations. These four examples could represent, respectively, yeasts, recombinant *E. coli*, Streptomyces, and mammalian cells. Many other examples are possible.

For example, if glutamine or the carbon-nitrogen source is in excess and is not growth limiting, then the pH control reagent is an acid, the ROMQ decreases monotonically with increasing glucose or carbon source concentration, and feedback control can be achieved using the preferred embodiment of the present invention. In this case, the growth rate will be a weak function of the carbon source concentration, and will not be zero in the absence of the carbon source due to the glutamine or the carbon-nitrogen source. However, the metabolic state will be a strong function of the growth rate. This often occurs during the growth phase of Streptomyces and other antibiotic processes.

Likewise, if glucose or the carbon source is in excess and is not growth limiting, then the ROMQ can be feedback-controlled by feeding glutamine or the carbon-nitrogen source.

The ROMQ may also decrease monotonically with increasing glucose or carbon source concentration during the stationary and death phases of many processes, including Streptomyces and other antibiotic processes. For example, during the growth phase the carbon source glucose may have been growth-limiting, but during the stationary and death phases growth may be limited by other factors. However, the organism consumes the glucose at the same rate it is fed, and completely oxidizes the excess glucose, causing the SOUR to increase, while spilling the excess energy. Thus, the metabolic state can be controlled by adjusting the glucose feed rate based on the ROMQ. By maintaining the ROMQ set point, the glucose feed rate will decrease with time in proportion to the decrease in the biomass concentration, i.e., the specific glucose uptake rate and the ammonia-glucose metabolic quotient (AGMQ) will be held constant during the stationary and death phases.

Or, ammonia, urea, nitrate, or other nitrogen sources can be used to limit growth and can be fed to control growth and metabolism.

Likewise, sulfate, phosphate, or other inorganic nutrients can be used to limit growth and can be fed to control growth and metabolism.

Or, for anaerobic processes, $CO_2$ or hydrogen evolution can be substituted for oxygen uptake, and a reagent-carbon dioxide or reagent-hydrogen metabolic quotient can be used in the same manner as the ROMQ in the preferred embodiment. Collectively, the oxygen uptake, $CO_2$ evolution, and hydrogen evolution rates are referred to as gas metabolic rates.

Also, although glucose was used as the fed carbon source in the examples, other carbon sources are equally applicable, including other carbohydrates, alcohols, organic acids, oils, and hydrocarbons. Likewise, although glutamine was used as the carbon-nitrogen source in the examples, other carbon-nitrogen sources are equally applicable, including other amino acids, peptides, and proteins.

Accordingly, the scope of the invention should be determined not by the three embodiments or four examples illustrated, but by the appended claims and their legal equivalents.

I claim:

1. A method of controlling the feed rate of a bioreactor in fed-batch and fed-batch perfusion fermentation and bioreactor processes, comprising the steps of:

a) measuring a pH control reagent addition rate and a gas metabolic rate selected from the group consisting of oxygen uptake, carbon dioxide evolution, and hydrogen evolution, b) calculating a ratio between said measured pH control reagent addition rate and said measured gas metabolic rate, c) comparing said ratio to a predetermined set point ratio that corresponds to a desired growth rate, and d) adjusting the feed rate of a feed containing at least a growth-limiting metabolite in order to maintain said ratio at said set point ratio, whereby feedback is used to maintain the growth rate of an organism at said desired growth rate.

2. The method of claim 1 wherein said gas metabolic rate is oxygen uptake, and wherein said desired growth rate is less than about one third of the maximum growth rate of said organism.

3. The method of claim 2 wherein said organism is a yeast.

4. The method of claim 1 wherein said gas metabolic rate is oxygen uptake, and wherein said desired growth rate is greater than about two thirds of the maximum growth rate of said organism, and wherein said organism produces an organic acid.

5. The method of claim 4 wherein said organism is a recombinant *Escherichia coli*.

6. The method of claim 1 wherein the feed contains a carbon source selected from the group consisting of glucose, other carbohydrates, alcohols, organic acids, oils, and hydrocarbons, and wherein the nitrogen source is ammonia.

* * * * *